United States Patent [19]
Battista et al.

[11] 3,954,493
[45] May 4, 1976

[54] REGENERATED CELLULOSE SPONGE

[75] Inventors: Orlando A. Battista; Richard L. Ward, both of Fort Worth, Tex.

[73] Assignee: Avicon, Inc., Fort Worth, Tex.

[22] Filed: May 20, 1974

[21] Appl. No.: 471,546

Related U.S. Application Data

[63] Continuation-in-part of Ser. No. 299,131, Oct. 19, 1972, abandoned.

[52] U.S. Cl. ............................... 106/127; 106/165
[51] Int. Cl.² ...................................... C08L 1/24
[58] Field of Search ........................... 106/165, 127

[56] References Cited
UNITED STATES PATENTS

| | | | |
|---|---|---|---|
| 3,364,036 | 1/1968 | Tesko | 106/208 |
| 3,649,331 | 3/1972 | Peterson | 106/122 |
| 3,649,347 | 3/1972 | Battista | 106/161 |

*Primary Examiner*—Theodore Morris

[57] ABSTRACT

Regenerated cellulose sponges of increased absorbency and rate of absorption formed by impregnating the sponge material with a solution or dispersion containing from 0.005% to 0.25% of a water-soluble or water-dispersible, high molecular weight, hydrophylic, film-forming polymer, drying the impregnated sponge and compressing it. The presence of the film-forming polymer allows the cutting of desired shaped individual sponges from the treated sponge material with a minimal formation of lint particles on the cut surfaces.

6 Claims, 1 Drawing Figure

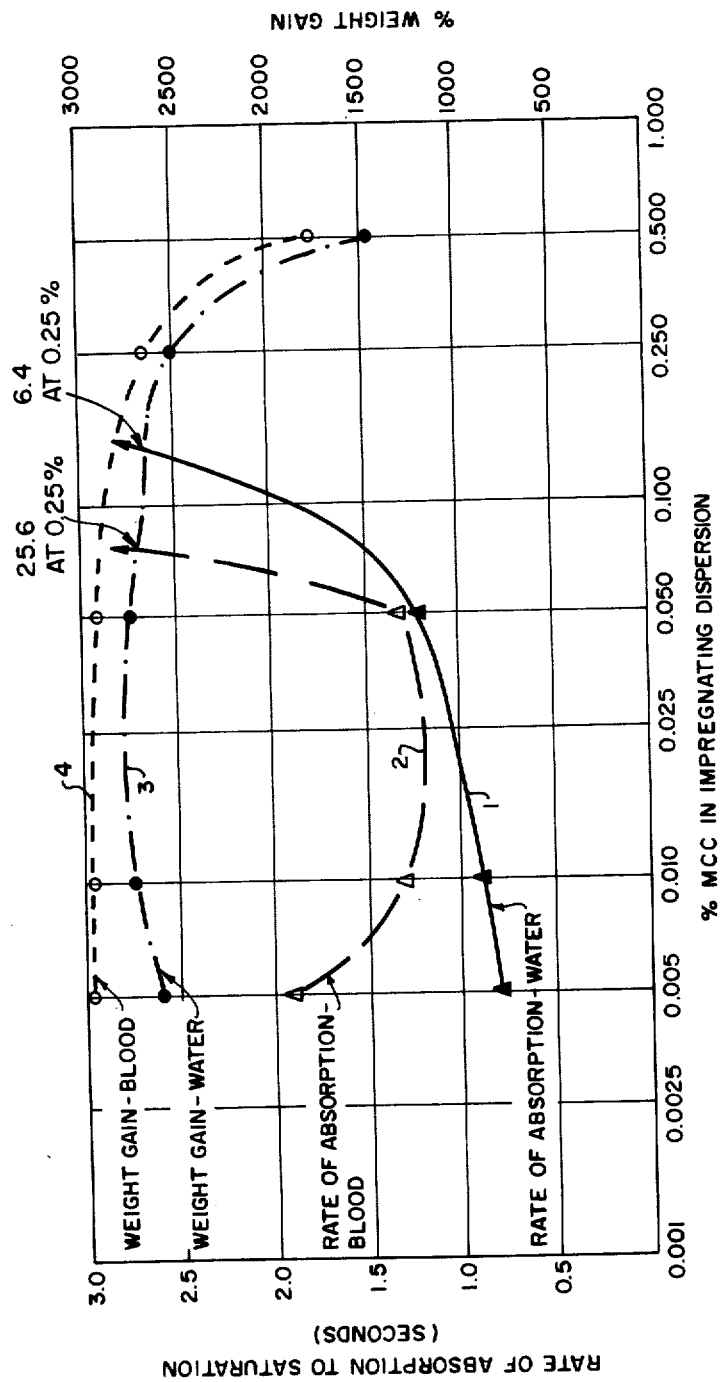

REGENERATED CELLULOSE SPONGE

This application is a continuation-in-part of our application Ser. No. 299,131 filed Oct. 19, 1972, now abandoned.

This invention relates to the production of artificial sponges and more specifically to artificial sponges adapted for use in surgical procedures and as topical wound dressings, feminine hygiene devices, for industrial purposes such as filters and desiccants and the like.

The sponges of this invention are based upon the well known artificial sponges comprising regenerated cellulose. As is well known the regenerated cellulose sponges are formed from a mixture of viscose, reinforcing fibers such as linen, jute, cotton, regenerated cellulose fibers and the like, and a pore forming constituent, generally crystals of sodium sulfate decahydrate or other alkali metal salt high in water of crystallization such as sodium acetate trihydrate, sodium carbonate decahydrate, trisodium phosphate dodecahydrate, disodium phosphate dodecahydrate, potassium sodium tartrate tetrahydrate and the like. In general, the viscous solution of viscose contains from 5 to 8% cellulose, 6 to 100% fibers, based on the cellulose, as reinforcing means and 900 to 2500% of the inorganic pore forming salt, based on the cellulose. The final pore size will be dependent upon the size of the pore forming inorganic salt crystals. The mixture is then introduced into desired molds or extruded through desired shaped orifices and the cellulosic solution coagulated and regenerated. After regeneration, the shaped mass is subjected to washing with water to remove the soluble salt and other constituents, desulphurized, bleached and, in general, finally treated with a solution of a plasticizer such as glycerol or propylene glycol. In view of the fact that the production of this type of artificial sponge is well known, it is deemed unnecessary to describe in further detail the production of such product.

There are at present several so-called surgical sponges which are utilized in various surgical procedures to absorb blood and body fluids. One of such devices formed of a polyurethane foam for use in ophthalmological surgical procedures is cut to a small spear-like shape from a sheet of the foam. Its principal disadvantage is the low rate of absorption of body fluids and blood and a relatively low liquid absorption characteristic. One of the advantages, however, is that in use this type of sponge is relatively free of lint along its surfaces. One type of surgical sponge of the common regenerated cellulose type is apparently formed by a thorough washing of regenerated cellulose sponge material to remove all soluble material including the plasticizer and after drying, compressing the sponge and cutting it to the desired size and shape, such as, a small spear-like or triangular shape. The spear type consists of a sponge head, triangular in shape about ¾ inch long, about ⅜ inch at its base, tapering to a rather fine point having a thickness of about 1/16 to ⅛ inch and having a molded plastic or wood handle secured to the base. These types of sponges absorb fluids including blood rapidly and have an appreciably higher absorbence than does the polyurethane type sponge. The principal disadvantage in the use of these types of sponges is that in the course of the cutting operation lint fragments are formed and, subsequently upon wetting, lint particles develop along the surfaces of the sponge. When used as in eye or ear surgery and in other surgical procedures and medical uses very fine particles of this lint frequently become dislodged and remain at the site of the sponge and thereby deposit at that site undesired foreign material (cellulose) which may not be visible to the naked eye.

In U.S. Pat. No. 3,018,192 there is described a method of improving the resistance of regenerated cellulose sponges to bacteria and fungi where the sponges are used for industrial purposes such as washing automobiles and the like. In this process the regenerated cellulose sponge is treated with an aqueous solution of carboxy methyl cellulose or an alkaline metal salt thereof and subsequently treated with a quaternary ammonium compound solution, the quaternary ammonium compound apparently reacting with the carboxy methyl cellulose to form a reaction product that is not removed by water, and, accordingly, is retained in the sponge during use. Alternatively, the regenerated cellulose sponge may first be treated with the quaternary ammonium compound solution followed by treatment with the carboxy methyl cellulose solution. In the only examples contained in the patent the sponges are treated with 1% by weight sodium carboxy methyl cellulose solutions and 1% by weight of a quaternary ammonium compound solutions. While these treatments will result in inhibiting the formation of lint on cut surfaces of the sponges, the rate of absorption of liquids and the amount of liquid absorbed by such treated sponges is so greatly reduced as compared to the untreated sponge that such products are not efficacious for uses as described herein.

One of the purposes of the present invention is to provide a method of treating regenerated cellulose sponge materials so as to reduce lint formation upon wetting.

Another purpose of the present invention is to provide a method of treating regenerated cellulose sponge so as to increase the rate of absorption of liquids and to improve the liquid absorbency of the treated sponges.

Another purpose of the invention is to provide a sponge which as a low or substantially negligible lint formation, comparable to that of polyurethane and other synthetic resin foams, and yet has a very rapid absorption characteristic and an improved liquid absorbency.

Further objects and advantages of the invention will become apparent from the description which follows in conjunction with the drawing which is a graph illustrating the critical relationship between the liquid absorption properties of the sponges and the polymer concentration of the impregnating solutions or dispersions.

The U.S. Pat. to Orlando A. Battista, No. 3,649,347, discloses structures having a self-adherent coating of a water-insoluble, water-dispersible, high molecular weight, hydrophylic, film-forming polymer, specifically, a water-insoluble, ionizable, partial acid salt of collagen having a bound ionizable acid content of from about 50 to about 90% of the stoichiometric bound acid content (microcrystalline collagen). Regenerated cellulose sponges were prepared in accordance with the disclosure of this patent.

EXAMPLE I

Sheets of commercially available white regenerated cellulose sponge of medium pore size (pores approximately 0.5 mm. to 3.5 mm.), compressed as received from a supplier, were immersed in water to thoroughly saturate the sponge sheets. The saturated sheets were washed with water so as to remove any soluble constituents. Each washed, water saturated sheet was then placed between sheets of aluminum foil and passed between rubber rollers of a hand wringer with its springs set at 3 inches so as to remove excess water. The sheets were then oven dried in a circulating air oven at a temperature of 75°C. for 90 minutes. The dried sponge sheets had an average thickness of approximately 7.5 mm. The dried sponge sheets were conditioned by maintaining them in the ambient atmosphere for 6 hours at a temperature of about 73°F. and a relative humidity of about 50%. The sponge sheets were subsequently compressed to an average thickness of approximately 1.2 mm. by pressing at about 24,000 psi in a Carver Press.

Triangular samples, designated as Samples A in Table 1, were cut with a scalpel from one of such compressed sponge sheets. The samples were approximately ¾ inch in length, about ⅜ inch at the base and tapered to a point.

Like triangular samples were cut from another compressed sheet. An aqueous dispersion of microcrystalline collagen (0.02% solids) was painted onto the top and bottom surfaces of the samples in an amount so as to completely wet the samples. The samples were dried in a circulating air oven at 75°C. for 90 minutes, conditioned for 6 hours at 73°F. and a relative humidity of about 50% and recompressed to a thickness of about 1.2 mm. The samples are designated as Samples B in Table 1. The recompression resulted in a spreading of the apex of the triangle and this distorted the original shape. The microcrystalline collagen was a partial HCl salt of collagen containing approximately 84% of the theoretical stoichiometric amount of HCl.

A like aqueous dispersion of microcrystalline collagen was painted onto the top and bottom surfaces of a dry, compressed sponge sheet. The sheet was dried, conditioned and recompressed as described in connection with the preparation of Samples B. Triangular samples, designated as Samples C in Table 1, were cut with a scalpel from the treated sheet.

Samples were saturated by immersion in water and allowed to fully expand. After removal from the water, excess water was allowed to drain and the cut sides of the samples were examined under a microscope at a magnification of 21X. The samples were arbitrarily graded on a scale of 0 – 10, where 0 indicates that the cut sides exhibited no visible lint projecting along the cut sides under the microscopic examination, and 10 indicating the cut sides exhibited a felt-like structure. Each individual particle of protruding lint was counted and given a score of 0.1. The average Lint Score from the samples is reported in Table 1.

Samples were weighed in the dry condition and subsequently saturated by immersion in water. The time for the samples to reach saturation (maximum expansion) was measured by the use of a stop watch. The rate of absorption is reported in Table 1 as the time in seconds to reach saturation. The samples were removed from the water, allowed to drain and re-weighed in a saturated condition. The percent of water absorbed was calculated from the dry and saturated weights.

Table 1

| Samples | Lint Score | Time to Saturation (Seconds) | Weight Gain (%) |
|---|---|---|---|
| A | 1.3 | 0.8 | 2470 |
| B | 10+ | 1.1 ± 0.2 | 1500.4 ±71.2 |
| C | 0.5 ± 0.03 | 0.6 ± 0.1 | 1719.9 ±20.8 |

It is obvious that by coating individual cut sponges with the film-former, the Lint Score is excessive and the rate of absorption is decreased. Where the sheet is coated and samples are cut from the recompressed sponge sheet the Lint Score is decreased and the rate of absorption is increased slightly. In both instances, the absorbency of the sponge samples is decreased appreciably.

The present invention is based upon the unexpected discovery that regenerated sponges of improved characteristics for the above-mentioned purposes may be prepared by saturating regenerated cellulose sponge material so as to uniformly distribute throughout the sponge a film-forming polymer whereas the coating of the sponge material results in a diminution of the characteristics particularly the absorbency of the sponge. These improved characteristics are attained by impregnating the sponge material with a solution or dispersion of a water-soluble or water-dispersible, high molecular weight, hydrophylic, film-forming polymer, the solution or dispersion containing from about 0.005% to about 0.250% by weight of the dissolved or dispersed polymer, drying the impregnated sponge and them compressing the dried sponge.

The sponges of the present invention may be prepared from commercial grades of regenerated cellulose sponge which are supplied either in expanded or in highly compressed form. Preferably, the regenerated cellulose sponge contains from 6 to 12% by weight of fibers. The average pore size of the dry, expanded sponge may vary from about 0.5 to about 3.5 mm., preferably averaging about 0.5 mm. to 1.5 mm., commonly referred to as "medium" pore size, particularly for medical and surgical purposes.

The sheets, as supplied, are saturated with water and are thoroughly washed with water to free them of soluble materials such as salts used in their preparation and any plasticizer which may be present. After thorough washing, excess water is removed by pressing or passing the saturated sponge between suitable rollers. The wet sponge is then saturated by immersion in a solution or dispersion of a water-soluble or water-dispersible, high molecular weight, hydrophylic, film-forming polymer. In order to thoroughly saturate and impregnate the sponge and distribute the film-forming polymer uniformly throughout the sponge, the sponge after immersion in the solution or dispersion is squeezed and released repeatedly while so immersed. This polymer may consist of carboxy methyl cellulose or an alkaline metal salt thereof such as sodium carboxy methyl cellulose, hydroxy ethyl cellulose, hydroxy-propylmethyl cellulose, methyl cellulose, regenerated cellulose derived from solutions of cellulose xanthate and cuprammonium cellulose, carageenen, starch, gelatin, collagen, microcrystalline collagen, polyvinyl alcohol, Carbopol, etc. Microcrystalline collagen is described in U.S. Pat. No. 3,628,974 and is a water-insoluble, ionizable, partial acid salt (preferably a hydrogen chloride salt) of collagen having a bound ionizable acid content of from about 50 to about 90% of the stoichiometric bound acid content, at least 10% by weight of the partial salt having a particle size under 1 micron. The solution or dispersion may contain from about 0.005 to about 0.250% by weight of the dissolved or dispersed polymer preferably 0.010 to 0.030% for medical and surgical purposes.

The excess liquid is removed from the saturated sponge sheet as by pressing and the sheet then dried as by oven drying at about 75°C. for about 1.5 hours. The specific drying conditions will be selected so as to provide a desired bonding between the film-forming polymer and the sponge base. Drying should be sufficient so that the dried sponge contains not more than about 0.5% volatiles including moisture. The dry sponge will contain between about 0.15% to about 5%, by weight, of the film-forming polymer, preferably for medical and surgical uses the film-former content is between 0.4 and 1.25%. The dried, uncompressed, treated sponge has a bulk density between about 2.5 and about 4.5 lbs./cu.ft.

Because of the inherent nature of the regenerated cellulosic sponge, it absorbs moisture from the atmosphere. In order to improve the dimensional stability of the pressed, impregnated sponge, the dried sponge is conditioned prior to compression. Conveniently, conditioning may be effected under normal atmospheric conditions by maintaining it at a temperature of about 73°F. and a relative humidity of about 50% to permit it to absorb atmospheric moisture. Obviously, other temperatures and conditions may be used. It has been discovered that where the sponge contains less than about 5% moisture at the time of final compression, the stability is poor and the sponge will absorb moisture and expand. The sponge is allowed to absorb at least about 6% moisture preferably 7 to 12% moisture prior to compression. After the sponge has absorbed an equilibrium proportion of moisture it is then compressed as at a pressure of about 20,000 to 24,000 psi using direct compression, as with a Carver Press. The compressed sponge has a bulk density between about 20 and 50 lbs./cu.ft. Thus, the compressed sponge for surgical procedures will have a bulk density of from about 4.5 to about 20 times that of the precursor sponge. For other uses such as tampons, tobacco smoke filters, absorbent pads for use in dentistry, the bulk density may be as low as about 7 lbs./cu.ft.; that is, the compressed sponge will have a bulk density of about 1.5 times that of the precursor sponge. Thus the product may have a bulk density of from about 7 lbs./cu.ft. to about 50 lbs./cu.ft. (1.5 to 20 times that of the precursor sponge) dependent upon the intended specific use of the product.

The invention may be further illustrated with reference to the following specific examples.

EXAMPLE II

Commercial yellow regenerated cellulose sponge of fine pore size (pores approximately 0.2 to 1.2 mm.) as received from the supplier was saturated in water and washed thoroughly to remove soluble constituents. The saturated sponge sheet was then placed between sheets of aluminum foil and passed between rubber rollers of a hand wringer with its springs set at 3 inches to remove the excess water. The sponge was then oven dried at 75°C. for 90 minutes. Upon removal from the oven the dry sponge which in expanded form was approximately 7.5 mm. in thickness was then compressed between the jaws of a vise to a thickness of about 1.2 mm.

EXAMPLE III

Commercial white regenerated cellulose sponge of medium pore size (pores approximately 0.5 to 3.5 mm.) as received in a highly compressed form from the supplier was treated as in Example II. The dry sponge of this example was approximately 15 mm. in thickness and was compressed to about 1.2 mm.

EXAMPLE IV

Commercial white regenerated cellulose sponge of medium pore size (pores approximately 0.5 to 3.5 mm.) was treated as in Example II. The dry sponge was approximately 7.5 mm. in thickness and was compressed to about 1.2 mm.

EXAMPLE V

Commercial white regenerated cellulose such as used in Example IV was saturated with water and washed with water to remove soluble constituents and after placing between aluminum foil sheets was passed through the rubber rollers as described in Example II so as to remove excess water. The wet sponge was then immersed and squeezed and released several times in a dispersion of microcrystalline collagen (partial salt of collagen containing approximately 84% of the theoretical stoichiometric amount of HCl), the dispersion containing 0.01% by weight of the microcrystalline collagen. The sheet was then removed from the dispersion, placed between sheets of aluminum foil and passed through the rubber rollers to remove excess water and oven dried at 75°C. for 90 minutes. Upon removal from the oven, the dry, impregnated sponge was compressed to a thickness of about 1.2 mm.

EXAMPLE VI

Commercial white regenerated cellulose as in Example IV was processed in the same manner as described in Example V substituting a gelatin solution containing 0.01% gelatin by weight for the microcrystalline collagen dispersion.

EXAMPLE VII

Commercial white regenerated cellulose sponge was treated as in Example V substituting a polyvinyl alcohol solution containing 0.01% by weight of polyvinyl alcohol for the microcrystalline collagen dispersion.

EXAMPLE VIII

Example V was repeated substituting a hydroxypropylmethyl cellulose solution containing 0.01% by weight of hydroxypropylmethyl cellulose for the microcrystalline dispersion.

EXAMPLE IX

Example V was repeated substituting a starch solution containing 0.01% by weight of starch for the microcrystalline collagen dispersion.

EXAMPLE X

This example consisted of a commercially available polyurethane surgical spear-shaped sponge.

EXAMPLES XI AND XII

These examples consisted of commercially available regenerated cellulose surgical spear-shaped sponges.

Spear shaped or triangular samples were cut from the products of each of Examples II through IX, the spears being approximately ¾ inch in length, about ⅜ of an inch at the base and tapering to a point, and approximately 1.2 mm. in thickness. The samples averaged approximately 40 mg. in weight. Samples of all of the foregoing examples were saturated by immersion in water and, after removal from the water and allowed to drain, the cut sides of the samples examined under a microscope at a magnification of about 21×. The samples were arbitrarily graded on a scale of 0 – 10, where 0 indicates that the cut sides were lint free; that is, no visible lint projected from along the sides of the spears under the microscopic examination, and 10 being felt-like in structure. Each individual particle of protruding lint was counted and given a score of 0.1. Sample spears were weighed in the dry condition and subsequently saturated by dropping a sample into water or blood (heparinized dog blood) and timing each sample to saturation; that is, maximum expansion, with a stop watch. The rate of absorption is reported as the time in seconds to reach saturation for the triangular samples which were about 40 mg. in weight. Each sample was removed from the water or blood, allowed to drain and re-weighed in a saturated condition. From the dry and saturated weights, the percent of liquid absorbed was calculated. These determined properties are set forth in Table 2.

Table 2

| Example | Lint Score | Time to Saturation (Seconds) | | Weight Gain (%) | |
|---|---|---|---|---|---|
| | | Water | Blood | Water | Blood |
| II | 3.0 | 0.9 | 3.3 | 1960 | 2150 |
| III | 1.8 | 1.4 | 3.6 | 1701 | 1971 |
| IV | 1.3 | 0.8 | 1.1 | 2470 | 2648 |
| V | 0.5 | 0.9 | 1.3 | 2735 | 2975 |
| VI | 0.5 | 0.8 | 1.5 | 2510 | 2798 |
| VII | 0.5 | 0.7 | 1.6 | 2668 | 2962 |
| VIII | 0.5 | 0.9 | 1.8 | 2930 | 2664 |
| IX | 0.4 | 1.1 | 1.4 | 2558 | 2623 |
| X | 0.5 | 10.6 | 10.1 | 1718 | 1971 |
| XI | 7.0 | 1.2 | 2.6 | 2305 | 1723 |
| XII | 7.25 | 1.8 | 3.2 | 2485 | 2889 |

EXAMPLE XIII

In order to illustrate the effect of the concentration of the film forming polymer in the impregnating solution or dispersion, Example V was repeated substituting for the 0.01% microcrystalline collagen dispersion, dispersions containing 0.50, 0.25, 0.05, 0.01, and 0.005% by weight microcrystalline collagen (MCC) dispersions. Examples of spears were examined under the microscope and the time to saturation and the weight gain of samples were determined and were as reported in Table 3.

Table 3

| Impregnating Dispersion % MCC | Lint Score | Time To Saturation (Seconds) | | Weight Gain (%) | |
|---|---|---|---|---|---|
| | | Water | Blood | Water | Blood |
| 0.50 | 0.4 | 33.7 | 71.4 | 1445 | 1741 |
| 0.25 | 0.4 | 6.4 | 25.6 | 2519 | 2640 |
| 0.05 | 0.5 | 1.2 | 1.3 | 2719 | 2920 |
| 0.01 | 0.5 | 0.9 | 1.3 | 2735 | 2975 |

Table 3-continued

| Impregnating Dispersion % MCC | Lint Score | Time To Saturation (Seconds) | | Weight Gain (%) | |
|---|---|---|---|---|---|
| | | Water | Blood | Water | Blood |
| 0.005 | 1.1 | 0.8 | 1.9 | 2585 | 2976 |

In order to more clearly illustrate the critical nature of the concentration of the film forming polymer solution used to saturate the sponge in its production, the data relating to the rate of absorption of the sponges and the percent weight gain of the sponges using the different concentrations in the dispersions are illustrated in the drawing. It will be noted from curves 1 and 2 that where the concentration of the impregnating solution exceeds about 0.05% the rate of absorption decreases rapidly. Where the concentration of the impregnating solution exceeds about 0.25% the percent weight gain or the absorbency of the sponges decreases rapidly as illustrated by curves 3 and 4.

Samples of sponges impregnated with dispersions containing 0.01, 0.02, and 0.05%, by weight, microcrystalline collagen were analyzed for nitrogen content and the collagen calculated from such analyses. The sponges contained 0.4, 1.0 and 1.4%, by weight, of collagen, respectively. Plotting these values illustrates that in the case of microcrystalline collagen, the binder content will vary from about 0.15 to about 2.5% where the impregnating liquid contains from about 0.005 to about 0.25% of microcrystalline collagen. For surgical uses, as in ophthalmological procedures where a high rate of absorption is required along with a high liquid absorbence, the preferred microcrystalline collagen content is between about 0.4 and about 1.25%, by weight. The specific binder content will vary within the broader range set forth hereinbefore depending upon the particular film-forming polymer.

EXAMPLE XIV

Example XIII was repeated using gelatin solutions as the impregnating solutions, the solutions containing 0.5, 0.25, 0.05, and 0.01% gelatin. Samples of sponges prepared from this film forming solution were rated as to lint formation, rate of absorption of water and blood, and the weight gain of water and blood. The results of these measurements on the various sponge samples are reported in Table 4.

Table 4

| Impregnating Solution % Gelatin | Lint Score | Time To Saturation (Seconds) | | Weight Gain (%) | |
|---|---|---|---|---|---|
| | | Water | Blood | Water | Blood |
| 0.50 | 0.4 | 1.5 | 3.9 | 2320 | 2585 |
| 0.25 | 0.5 | 1.3 | 3.6 | 2583 | 2602 |
| 0.05 | 0.5 | 1.1 | 1.7 | 2692 | 2723 |
| 0.01 | 0.6 | 0.8 | 1.6 | 2510 | 2798 |

EXAMPLE XV

Example XIII was repeated substituting for the microcrystalline collagen dispersions of polyvinyl alcohol containing 0.1 and 0.01% polyvinyl alcohol (PVA) by weight. Samples of products produced using these impregnating solutions were examined for lint, rate of absorption of water and blood and weight gain of water and blood. These properties are reported in Table 5.

Table 5

| Impregnating Solution % PVA | Lint Score | Time to Saturation (Seconds) | | Weight Gain (%) | |
|---|---|---|---|---|---|
| | | Water | Blood | Water | Blood |
| 0.10 | 0.5 | 8.8 | 40.4 | 3278 | 3001 |
| 0.01 | 0.5 | 0.7 | 1.6 | 2668 | 2962 |

It is obvious that other film-forming polymers may be utilized in the same manner as illustrated by the foregoing specific examples. For example, in comparison to gelatin, collagen is heat coagulable, dries faster to form a nontacky tougher and less brittle coating than gelatin. Whereas gelatin swells and softens on contact with water, dried collagen films are substantially unaffected by water. Acidic dispersions of collagen fibrils such as dispersions in solutions of acetic, citric, lactic, cyanoacetic and malonic acids may be substituted for the gelatin solutions and microcrystalline collagen dispersions to form products of like properties. Procollagen and collagen fibril gels and dispersions are well known and, for example, may be repeated in accordance with U.S. Pat. Nos. 2,838,363 and 2,920,000.

Similarly, regenerated cellulose as derived frm viscose and cuprammonium cellulose solutions may be used to form products having like properties. For example, in the use of viscose, the viscose as conventionally prepared for the production of rayon or cellophane usually containing between 5 and 8% cellulose is diluted to the required cellulose content (0.005 to 0.250%). The washed sponge is impregnated with the dilute viscose solution and the excess liquid removed as by pressing. The viscose retained in the sponge is coagulated, the alkalie neutralized and the cellulose regenerated by immersing the sponge in dilute sulfuric acid. If desired, the regenerated cellulose may be desulfurized and bleached and after removing excess liquid, the sponge is thoroughly washed to remove soluble substances until the wash water is neutral. Excess water is removed, the sponge dried and compressed to the desired bulk density as described hereinbefore. If desired, particularly where the sponge is intended for industrial purposes, cuprammonium cellulose solutions may be substituted for the viscose solutions.

As is obvious from the foregoing description, the specific film-forming polymer and the amount may be selected based upon the intended use of the specific sponge and similarly the degree of compression will be selected on the basis of the use of the sponge. For example, in the case of disposable sponges for use in eye and ear surgery the collagenous binders are used in the lower portion of the range and high compression is preferred. For use in dental procedures and tobacco smoke filters, lower compression is preferred. In sealed refrigeration systems containing a refrigerant such as Freon and oil as a lubricant the presence of moisture is detrimental in that the moisture freezes at the expansion orifice thereby rendering the system inoperative or greatly reducing the cooling effect. In such system, the sponge is used as a more or less permanent filter and desiccant through which the liquid passes. In such use regenerated cellulose may be utilized and the amount may be in the upper portion of the range and the sponge is preferably in highly compressed form. For use as a wound dressing, microcrystalline collagen is preferred because of its hemostatic properties and may be used in the higher amounts. Obviously, other uses as a filter medium and desiccant will suggest themselves to the skilled artisan.

What is claimed is:

1. A compressed regenerated cellulose sponge consisting essentially of regenerated cellulose and from about 0.15 to about 2.5% of a water-soluble or water-dispersible, high molecular weight, hydrophylic, film-forming polymer uniformly distributed throughout the sponge, the sponge being characterized in absorbing at least 25 times its weight of water and having a bulk density of at least 7 lbs./cu. ft. and, in contrast to a like regenerated cellulose sponge free of such film-forming polymer, exhibiting an increased liquid absorbency and, upon wetting, exhibiting a reduced lint formation along cut surfaces and, in contrast to a like regenerated cellulose sponge coated with such film-forming polymer, exhibiting an increased liquid absorbency.

2. A compressed regenerated cellulose sponge as defined in claim 1 wherein the compressed sponge has a bulk density of between about 7 lbs./cu.ft. and 50 lbs./cu.ft.

3. A compressed regenerated cellulose sponge as defined in claim 2 containing about 0.4 to about 1.25% of the film-forming polymer.

4. A compressed regenerated cellulose sponge as defined in claim 1 wherein the film-forming polymer is regenerated cellulose.

5. A compressed regenerated cellulose sponge as defined in claim 1 wherein the the film-forming polymer is microcrystalline collagen.

6. A compressed regenerated cellulose sponge as defined in claim 1 wherein the film-forming polymer is gelatin.

* * * * *